US00PP14723P2

(12) United States Plant Patent
Hofmann

(10) Patent No.: US PP14,723 P2
(45) Date of Patent: Apr. 20, 2004

(54) NEW GUINEA IMPATIENS PLANT NAMED 'FISNICS WHITE'

(50) Latin Name: *Impatiens hawkeri*
Varietal Denomination: Fisnics White

(76) Inventor: Birgit Christa Hofmann, Gassenweg 29, 56170 Bendorf (DE)

( * ) Notice: Subject to any disclaimer, the term of this patent is extended or adjusted under 35 U.S.C. 154(b) by 0 days.

(21) Appl. No.: 10/452,978

(22) Filed: Jun. 3, 2003

(51) Int. Cl.[7] ..... A01H 5/00

(52) U.S. Cl. ..... Plt./318
(58) Field of Search ..... Plt./318

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea Impatiens plant named 'Fisnics White', characterized by its outwardly spreading and uniformly mounded plant habit; small to medium growth habit; freely branching and freely flowering habit; deep green-colored foliage; and large, rounded and white-colored flowers that are positioned above and beyond the foliage.

1 Drawing Sheet

Botanical classification/cultivar designation: *Impatiens hawkeri* cultivar Fisnics White.

BACKGROUND OF THE INVENTION

The present Invention relates to a new and distinct cultivar of New Guinea Impatiens plant, botanically known as *Impatiens hawkeri*, and hereinafter referred to by the name 'Fisnics White'.

The new Impatiens is a product of a planned breeding program conducted by the Inventor in Hillscheid, Germany and Moncarapacho, Portugal. The objective of the breeding program is to develop new medium-sized Impatiens cultivars with an early to medium flowering response and large rounded flowers with attractive coloration.

The new Impatiens originated from a cross-pollination made by the Inventor during the summer of 1998 of a proprietary seedling selection of *Impatiens hawkeri* identified as code number K98-4069-21, not patented, as the female, or seed, parent with the *Impatiens hawkeri* cultivar Danisu, not patented, as the male, or pollen, parent. The cultivar Fisnics White was discovered and selected by the Inventor as a flowering plant within the progeny of the stated cross-pollination in a controlled environment in Moncarapacho, Portugal in April, 1999.

Asexual reproduction of the new cultivar by terminal cuttings taken in Moncarapacho, Portugal, since July, 1999, has shown that the unique features of this new Impatiens are stable and reproduced true to type in successive generations.

SUMMARY OF THE INVENTION

The following traits have been repeatedly observed and are determined to be the unique characteristics of 'Fisnics White'. These characteristics in combination distinguish 'Fisnics White' as a new and distinct Impatiens cultivar:

1. Outwardly spreading and uniformly mounded plant habit; small to medium growth habit.
2. Freely branching and freely flowering habit.
3. Deep green-colored foliage.
4. Large, rounded and white-colored flowers that are positioned above and beyond the foliage.

Plants of the new Impatiens can be compared to plants of the female parent selection. In side-by-side comparisons conducted by the Inventor in Hillscheid, Germany, plants of the new Impatiens differed from plants of the female parent selection in the following characteristics:

1. Flower spurs of plants of the new Impatiens were white to pale light green in color whereas flower spurs of plants of the female parent selection were light pink in color.
2. Flowers of plants of the new Impatiens were white in color whereas flowers of plants of the female parent selection were white with a faint red purple hue.

Plants of the new Impatiens can be compared to plants of the male parent, the cultivar Danisu. In side-by-side comparisons conducted by the Inventor in Hillscheid, Germany, plants of the new Impatiens differed from plants of the cultivar Danisu in the following characteristics:

1. Plants of the new Impatiens were not as broad as plants of the cultivar Danisu.
2. Leaves of plants of the new Impatiens were smaller, darker green in color and had shorter petioles than plants of the cultivar Danisu.
3. Flowers of plants of the new Impatiens were larger and were held higher above the foliage than flowers of plants of the cultivar Danisu.

Plants of the new Impatiens can also be compared to plants of the cultivar Moorea, disclosed in U.S. Plant Pat. No. 9,147. In side-by-side comparisons conducted by the Inventor in Hillscheid, Germany, plants of the new Impatiens differed from plants of the cultivar Moorea in the following characteristics:

1. Plants of the new Impatiens had darker green-colored leaves than plants of the cultivar Moorea.
2. Flower spurs of plants of the new Impatiens were white to pale light green in color whereas flower spurs of plants of the cultivar Moorea were white to light pink in color.
3. Plants of the new Impatiens had larger flowers than plants of the cultivar Moorea.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Fisnics White' grown in a container.

DETAILED BOTANICAL DESCRIPTION

The cultivar Fisnics White has not been observed under all possible environmental conditions. The phenotype may vary somewhat with variations in environment such as temperature and light intensity, without, however, any variance in genotype.

The aforementioned photograph, following observations and measurements describe plants grown in Hillscheid, Germany, under commercial production practice in a glass-covered greenhouse. Rooted young plants were planted in 12-cm containers in late February and the aforementioned photograph and following observations and measurements were taken about 11 weeks later in early May. During the production of the plants, day temperatures were about 18 to 22° C. and night temperatures were about 16 to 18° C. In the following description, color references are made to The Royal Horticultural Society Colour Chart, 1995 Edition, except where general terms of ordinary dictionary significance are used.

Botanical classification: *Impatiens hawkeri* cultivar Fisnics White.

Parentage:

*Female parent.*—Proprietary seedling selection of *Impatiens hawkeri* identified as code number K98-4069-21, not patented.

*Male parent.*—*Impatiens hawkeri* cultivar Danisu, not patented.

Propagation:

*Type cutting.*—Terminal tip cuttings.

*Time to initiate roots.*—Summer: About 8 to 10 days at 24° C. Winter: About 12 to 15 days at 21° C.

*Time to produce a rooted cutting.*—Summer: About 15 days at 24° C. Winter: About 18 to 20 days at 21° C.

*Root description.*—Numerous, fibrous, and freely branching; 158D in color.

Plant description:

*General appearance.*—Outwardly spreading and uniformly mounded plant growth habit; small to medium growth habit; freely branching habit, dense and bushy appearance; freely flowering. Moderately vigorous.

*Crop time.*—From a rooted cutting, about 9 to 10 weeks are required to produce finished flowering plants in 12-cm containers.

*Plant height.*—About 12 to 15 cm.

*Plant diameter or spread.*—About 33 to 38 cm.

*Lateral branches.*—Quantity per plant: About 10. Length: About 11 to 13 cm. Diameter: About 7 mm. Internode length: About 3.5 to 4 cm. Texture: Smooth, glabrous. Color: 143C.

*Foliage description.*—Arrangement: Primarily in whorls. Length: About 12 cm. Width: About 4.5 cm. Shape: Elliptic to narrowly ovate. Apex: Acute to acuminate. Base: Acute. Margin: Serrulate with ciliation. Texture: Smooth, slightly rugose; glabrous. Color: Developing foliage, upper surface: 143A. Developing foliage, lower surface: 138B. Fully expanded foliage, upper surface: 137A. Fully expanded foliage, lower surface: 138B. Venation, upper and lower surfaces: 145C. Petiole: Length: About 1 to 1.5 cm. Diameter: About 3 to 4 mm. Texture: Smooth, glabrous. Color, upper surface: 158A. Color, lower surface: 157A.

Flower description:

*Flower type and flowering habit.*—Single, large, rounded, and white-colored flowers. Freely and continuously flowering; usually about 7 to 9 flowers and flower buds per lateral branch. Flowers positioned above and beyond the foliage; flowers typically face parallel to the leaf canopy. Petals not persistent; gynoecium persistent. Flowers not fragrant.

*Flower longevity.*—Flowers last about 8 to 9 days on the plant.

*Flowering season.*—Year-round under greenhouse conditions. Plants begin flowering about 8 to 9 weeks after planting.

*Flower buds.*—Length: About 2.2 cm. Diameter: About 1.6 cm. Shape: Ovoid. Color: 158C.

*Flower length.*—About 7.6 cm.

*Flower width.*—About 7.5 cm.

*Flower depth.*—About 1 cm.

*Petals.*—Quantity: Five per flower, imbricate. Length: Banner petals: About 3.3 to 3.5 cm. Lateral and base petals: About 4 to 4.5 cm. Width: Banner petal: About 4.5 to 4.6 cm. Lateral petals: About 3 to 3.2 cm. Basal petals: About 3.7 to 3.8 cm. Shape: Cordate. Apex: Weakly to moderately lobed; emarginate. Base: Attenuate. Margin: Entire. Aspect: Mostly flat. Texture: Smooth; satiny. Color: When opening and fully opened, upper surface: 155D. When opening and fully opened, lower surface: 155D; occasionally, a faint small red purple, 68D, eye zone.

*Spur.*—Quantity: One per flower. Length: About 6.5 to 7 cm. Diameter: At apex: About 0.5 mm. At flower: About 3 mm. Aspect: Curved. Color: 155A to 145D.

*Peduncles.*—Length: About 5 to 5.5 cm. Diameter: About 2 mm. Texture: Smooth, glabrous. Strength: Strong, flexible. Color: 145B.

*Reproductive organs.*—Androecium: Stamen number: Five fused at anthers, hooded; filaments free. Anther length: About 6 mm. Anther shape: Obovate. Anther color: 155A to 158A. Pollen amount: Moderate. Pollen color: 8D. Gynoecium: Pistil quantity: One per flower. Pistil length: About 5 to 6 mm. Stigma color: 150D. Style color: 150D. Ovary: Five-celled. Ovary color: 143C.

*Seed/fruit.*—Seed and fruit development has not been observed.

Disease/pest resistance: Plants of the new Impatiens have not been observed to be resistant to pathogens and pests common to Impatiens.

Low temperature tolerance: Plants of the new Impatiens have been observed to tolerate night temperatures of 5° C. with 10° C. day temperatures.

It is claimed:

1. A new and distinct cultivar of New Guinea Impatiens plant named 'Fisnics White', as illustrated and described.

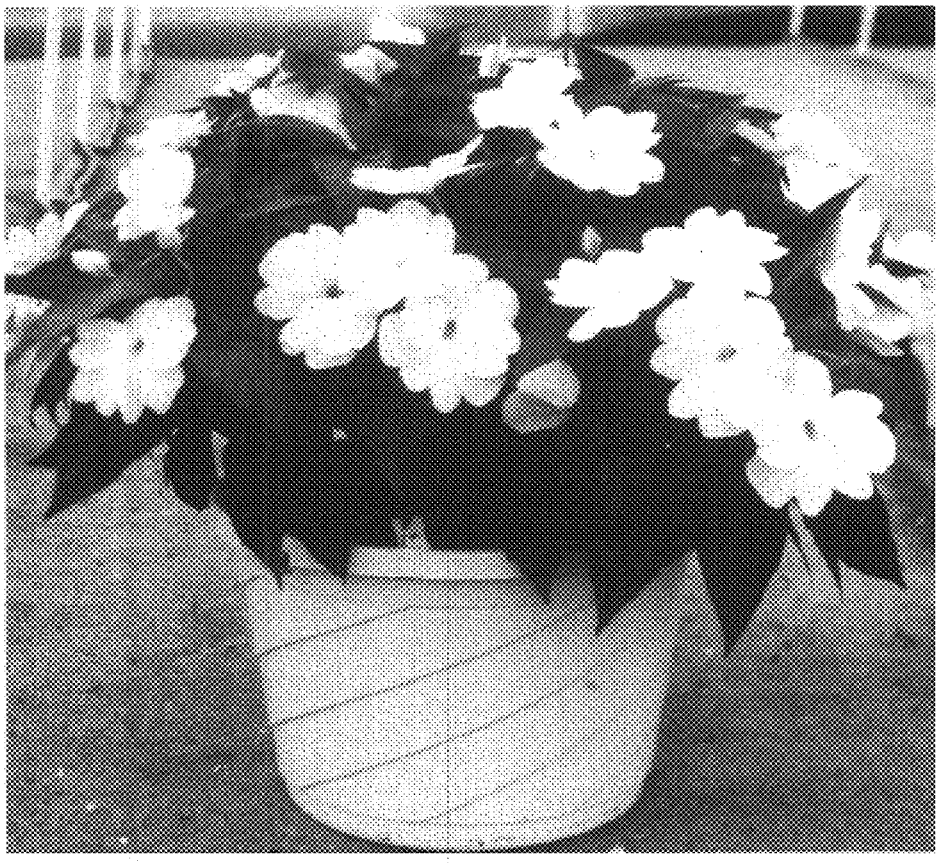

* * * * *